United States Patent
Yamaguchi

(10) Patent No.: US 12,246,728 B2
(45) Date of Patent: Mar. 11, 2025

(54) SAFE DRIVING DETERMINATION APPARATUS

(71) Applicant: ISUZU MOTORS LIMITED, Tokyo (JP)

(72) Inventor: Kazuhiko Yamaguchi, Fujisawa (JP)

(73) Assignee: ISUZU MOTORS LIMITED, Tokyo (JP)

( * ) Notice: Subject to any disclaimer, the term of this patent is extended or adjusted under 35 U.S.C. 154(b) by 274 days.

(21) Appl. No.: 17/908,911

(22) PCT Filed: Mar. 9, 2021

(86) PCT No.: PCT/JP2021/009367
§ 371 (c)(1),
(2) Date: Sep. 1, 2022

(87) PCT Pub. No.: WO2021/182483
PCT Pub. Date: Sep. 16, 2021

(65) Prior Publication Data
US 2023/0100810 A1 Mar. 30, 2023

(30) Foreign Application Priority Data
Mar. 11, 2020 (JP) ................................ 2020-042077

(51) Int. Cl.
*B60W 40/09* (2012.01)
*B60W 40/105* (2012.01)
(Continued)

(52) U.S. Cl.
CPC .......... *B60W 40/09* (2013.01); *B60W 40/105* (2013.01); *B60W 50/14* (2013.01);
(Continued)

(58) Field of Classification Search
CPC .... B60W 40/09; B60W 40/105; B60W 50/14; B60W 2540/229; B60W 2420/403; G06V 20/597
See application file for complete search history.

(56) References Cited

U.S. PATENT DOCUMENTS 5,867,587 A * 2/1999 Aboutalib .............. G08B 21/06
340/576
6,028,608 A * 2/2000 Jenkins ................... G06T 15/00
345/619
(Continued)

FOREIGN PATENT DOCUMENTS

| CN | 109774723 A | 5/2019 |
| JP | 2010-257293 A | 11/2010 |

(Continued)

OTHER PUBLICATIONS

Zhou Ming et al., "Research on the cause of the accident analysis and countermeasure of heavy duty truck right." Automobile Applied Technology, 2017 No. 9. Published May 15, 2017. CNKI, Document Code A, Article ID: 1671-7988 (2017)09-84-04. DOI: 10.16638/j.cnki.1671-7988.2017.09.031. 4 pages.

*Primary Examiner* — Luis A Martinez Borrero
(74) *Attorney, Agent, or Firm* — PROCOPIO, CORY, HARGREAVES & SAVITCH LLP

(57) ABSTRACT

A safe driving determination apparatus includes an angle value calculation part that calculates an angle value indicating a face direction angle of a driver with respect to the traveling direction, and a determination part that determines whether or not the driver is in a state of being inattentive to the road ahead on the basis of whether or not an integrated value of angle values during a past predetermined first determination period is equal to or greater than a threshold value, wherein the determination part does not determine that the driver is in a state of being inattentive to the road (Continued)

ahead if the angle value of the driver is less than a second threshold value at the present moment, even if an integrated value of angle values during a past predetermined first determination period is equal to or greater than a first threshold value.

6 Claims, 5 Drawing Sheets

(51) Int. Cl.
    *B60W 50/14*     (2020.01)
    *G06V 20/59*     (2022.01)

(52) U.S. Cl.
    CPC ..... *G06V 20/597* (2022.01); *B60W 2420/403* (2013.01); *B60W 2540/229* (2020.02)

(56) References Cited

U.S. PATENT DOCUMENTS

| | | | |
|---|---|---|---|
| 6,091,334 A * | 7/2000 | Galiana | G08B 21/06 340/576 |
| 6,097,295 A * | 8/2000 | Griesinger | A61B 5/18 340/576 |
| 7,027,621 B1 * | 4/2006 | Prokoski | G06V 40/165 340/576 |
| 9,248,796 B2 * | 2/2016 | Takahashi | G01C 21/3602 |
| 9,460,601 B2 * | 10/2016 | Mimar | G08B 21/06 |
| 10,640,122 B2 * | 5/2020 | Kishi | B60W 40/08 |
| 10,723,365 B2 * | 7/2020 | Kume | B60K 35/29 |
| 11,443,534 B2 * | 9/2022 | Takinami | B60Q 9/00 |
| 11,661,075 B2 * | 5/2023 | Julian | G06V 40/19 340/439 |
| 11,861,916 B2 * | 1/2024 | Vedantam | G06V 10/25 |
| 11,993,277 B2 * | 5/2024 | Julian | G08G 1/164 |
| 2003/0146841 A1 * | 8/2003 | Koenig | A61B 5/18 340/576 |
| 2005/0073136 A1 * | 4/2005 | Larsson | A61B 5/11 180/272 |
| 2010/0033333 A1 * | 2/2010 | Victor | A61B 5/7264 340/576 |
| 2014/0139655 A1 * | 5/2014 | Mimar | G08B 21/0476 340/575 |
| 2015/0094907 A1 * | 4/2015 | Offenhaeuser | A61B 5/18 600/549 |
| 2017/0313319 A1 * | 11/2017 | Kishi | G06V 20/597 |
| 2019/0102638 A1 * | 4/2019 | Nanu | G06T 7/50 |
| 2019/0147265 A1 * | 5/2019 | Aizawa | G06V 10/96 382/103 |
| 2019/0147269 A1 | 5/2019 | Aoi et al. | |
| 2019/0283764 A1 * | 9/2019 | Morimoto | G06F 3/012 |
| 2019/0337533 A1 * | 11/2019 | Kume | B60K 35/28 |
| 2021/0081754 A1 * | 3/2021 | Frolova | G06N 3/04 |
| 2021/0347365 A1 * | 11/2021 | Yamaguchi | G08G 1/16 |
| 2021/0350155 A1 * | 11/2021 | Takinami | B60W 50/14 |
| 2021/0394775 A1 * | 12/2021 | Julian | B60W 50/14 |
| 2022/0058407 A1 * | 2/2022 | Yang | G06T 7/30 |
| 2022/0284718 A1 * | 9/2022 | Kurokawa | G06V 10/62 |
| 2022/0301323 A1 * | 9/2022 | Matsumura | G06V 40/18 |
| 2023/0227058 A1 * | 7/2023 | Julian | B60W 50/14 340/439 |

FOREIGN PATENT DOCUMENTS

| | | |
|---|---|---|
| JP | 2012-084068 A | 4/2012 |
| JP | 2016-018304 A | 2/2016 |
| JP | 2016-081087 A | 5/2016 |
| JP | 2016-207174 A | 12/2016 |
| JP | 6565305 B | 8/2019 |

* cited by examiner

SAFE DRIVING DETERMINATION APPARATUS

CROSS-REFERENCE TO RELATED APPLICATIONS

The present application is a U.S. National Stage entry of PCT Application number PCT/JP2021/009367, filed on Mar. 9, 2021, which claims priority under 35 U.S.C § 119(a) to Japanese Patent Application No. 2020-042077, filed on Mar. 11, 2020, contents of which are incorporated herein by reference in their entirety.

TECHNICAL FIELD

The present disclosure relates to a safe driving determination apparatus.

BACKGROUND ART

Conventionally, an apparatus has been proposed that determines whether a driver is inattentive to the road ahead (looking aside) according to a face direction of a driver while driving a vehicle, and alerts the driver if the driver is determined to be inattentive to the road ahead. Patent document 1 discloses a device for determining a state of being inattentive that determines whether a driver is inattentive to the road ahead on the basis of a difference between i) a reference value and ii) an integrated value obtained by time-integrating a difference between a) a driver's face direction and b) a traveling direction of the vehicle over a certain period of time in the past.

PRIOR ART

Patent Document

Patent Document 1: Japanese Patent No. 6565305

SUMMARY OF INVENTION

Problems to be Solved by the Invention

A conventional device for determining a state of being inattentive prevents or reduces an erroneous determination that a behavior similar to a behavior of being inattentive to the road ahead, such as checking a mirror, is inattentive to the road ahead, by using the integrated value of a driver's face direction for a certain period of time in the past. However, if the integrated value in the past is greater than the reference value, the conventional device for determining a state of being inattentive determines that the driver is inattentive to the road ahead, even if the driver is not inattentive to the road ahead at the present moment.

The present disclosure focuses on this point, and an object thereof is to prevent or reduce an issuance of an alarm if the driver is not in a state of being inattentive to the road ahead at the present moment, even if the driver was in a state of being inattentive to the road ahead during a certain period of time in the past.

Means for Solving the Problems

A safe driving determination apparatus according to an embodiment of the present disclosure is a safe driving determination apparatus for acquiring an angle value indicating a face direction angle of a driver by using a traveling direction of a vehicle as a reference after capturing an image of the driver of the vehicle with an imaging device to determine whether or not the driver is in a state of being inattentive to the road ahead on the basis of the acquired angle value, the apparatus includes an angle value calculation part that calculates an angle value indicating a face direction angle of at least one of i) a face direction angle of the driver in a yaw direction with respect to the traveling direction or ii) a face direction angle of the driver in a pitch direction with respect to the traveling direction, and a determination part that determines whether or not the driver is in a state of being inattentive to the road ahead on the basis of whether or not an integrated value of angle values during a past predetermined first determination period is equal to or greater than a threshold value, wherein the determination part i) determines that the driver is in a state of being inattentive to the road ahead if an integrated value of angle values during a past predetermined first determination period is equal to or greater than a first threshold value and the angle value of the driver is equal to or greater than a second threshold value at the present moment, and ii) does not determine that the driver is in a state of being inattentive to the road ahead if the angle value of the driver is less than a second threshold value at the present moment, even if an integrated value of angle values during a past predetermined first determination period is equal to or greater than a first threshold value.

The determination part may determine whether or not the driver is in a state of being inattentive to the road ahead on the basis of a result of comparing a statistic value of a plurality of the angle values within a second determination period including the present moment with a third threshold value.

The determination part may determine whether or not the driver is in a state of being inattentive to the road ahead on the basis of a result of comparing the statistic value of the plurality of angle values in the second determination period, which is shorter than the first determination period and includes the present moment, with the third threshold value.

If the statistical value of the plurality of angle values in the second determination period is less than the third threshold value, the determination part does not have to determine that the driver is in a state of being inattentive to the road ahead even if the angle value is equal to or greater than the first threshold value.

The determination part may determine a length of the second determination period on the basis of the speed of the vehicle at the present moment.

The determination part may determine a length of the second determination period to be shorter when the speed of the vehicle is high than when the speed of the vehicle is low.

The determination part may determine the third threshold value on the basis of the speed of the vehicle at the present moment.

The determination part may set the third threshold value smaller when the speed of the vehicle is high than when the speed of the vehicle is low.

Effect of the Invention

According to the present disclosure, it is possible to prevent or reduce an issuance of an alarm if the driver is not in a state of being inattentive to the road ahead at the present moment, even if the driver was in a state of being inattentive to the road ahead during a certain period of time in the past.

DESCRIPTION OF EMBODIMENTS

<Configuration of Vehicle S>

Figure 1:
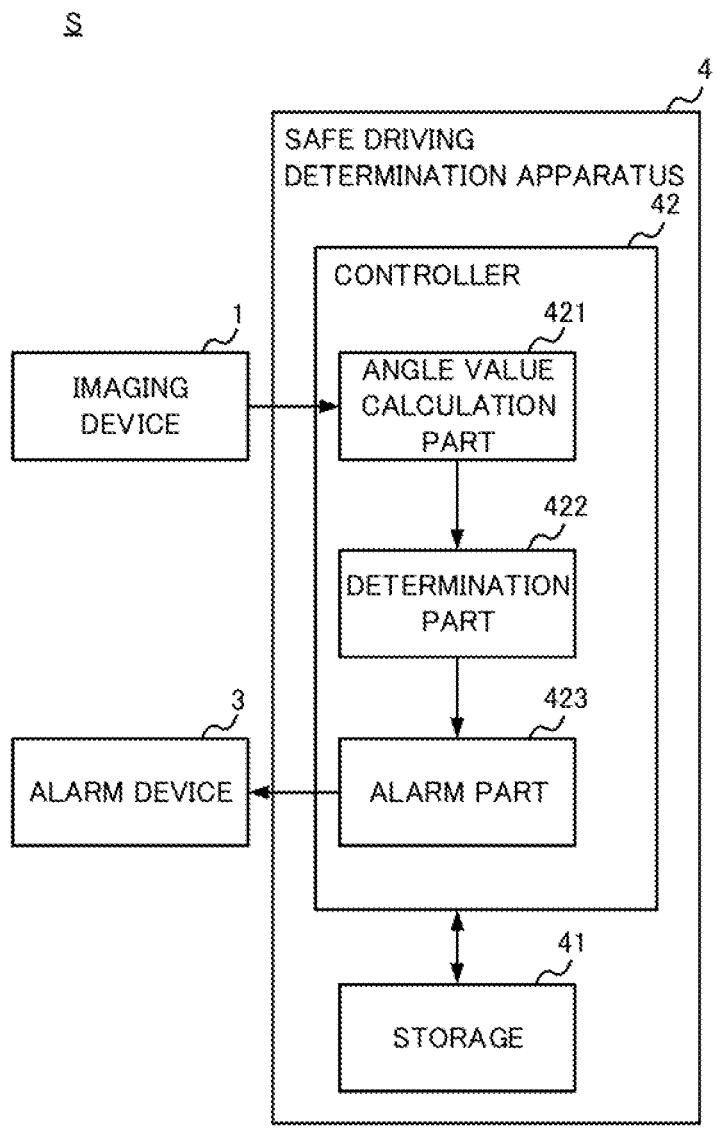
FIG. 1 shows a configuration of a vehicle S according to the present disclosure.

FIG. 1 shows a configuration of a vehicle S according to the present disclosure. The vehicle S includes an imaging device 1, an alarm device 3, and a safe driving determination apparatus 4.

The imaging device 1 is provided to a driver's seat of the vehicle S, and includes a CCD camera, for example. The imaging device 1 captures an image of a driver sitting in the driver's seat from the front to generate a captured image. For example, the imaging device 1 captures an image of a driver's face while the vehicle S is traveling, and generates the captured image that enables identification of the driver's face direction angle with respect to the traveling direction of the vehicle S. The imaging device 1 outputs the generated captured image to the safe driving determination apparatus 4.

Figure 2A:
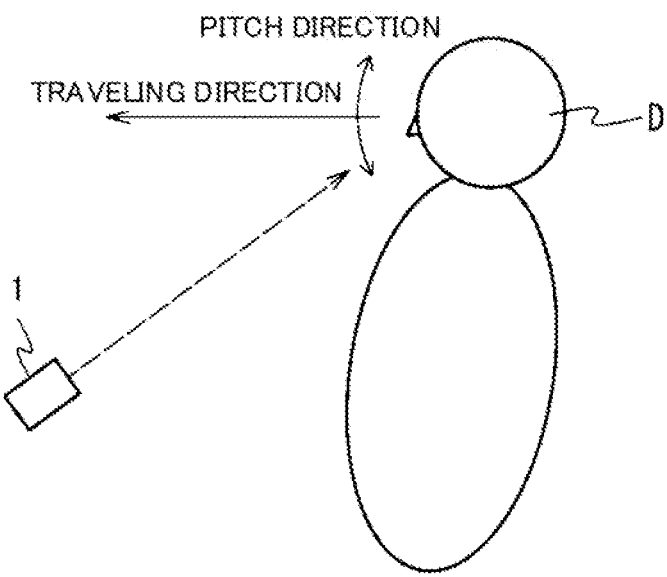
FIG. 2A shows a relationship between an imaging device 1 and a driver's face angle.
Figure 2B:
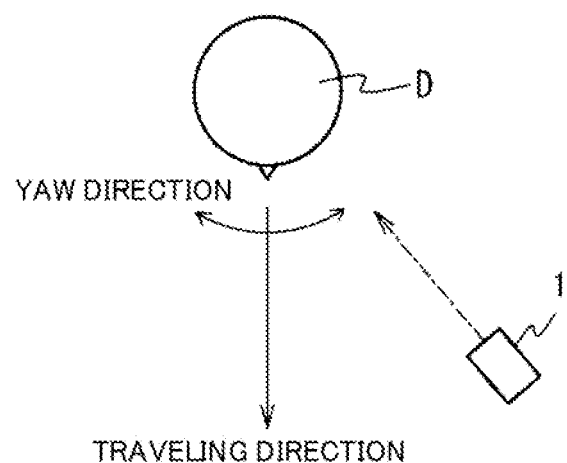
FIG. 2B shows a relationship between an imaging device 1 and a driver's face angle.

FIGS. 2A and 2B show a relationship between the imaging device 1 and a driver's face angle. FIG. 2A shows a side view of a driver D, and FIG. 2B shows a top view of the driver D. As shown in FIGS. 2A and 2B, the imaging device 1 is not in front of a driver D's face, but is provided diagonally downward from the driver D's face, for example.

The alarm device 3 is a device that issues an alarm to the driver on the basis of notification from the safe driving determination apparatus 4 that the driver is inattentive to the road ahead (for example, looking aside) while driving. The alarm device 3 includes a speaker for issuing an alarm, a display part for displaying a warning screen, and a vibration generation part for generating vibration, for example. It should be noted that the alarm device 3 may issue the alarm by combining at least two of sound, display, and vibration.

The safe driving determination apparatus 4 includes a storage 41 and a controller 42. The safe driving determination apparatus 4 captures the image of the driver of the vehicle S using the imaging device 1 to identify an angle value indicating the driver's face direction angle when referenced to the traveling direction of the vehicle. The safe driving determination apparatus 4 determines whether or not the driver is in a state of being inattentive to the road ahead on the basis of the acquired angle value. If the safe driving determination apparatus 4 determines that the driver is in the state of being inattentive to the road ahead, the safe driving determination apparatus 4 notifies the alarm device 3 to issue the alarm.

The storage 41 includes a storage medium such as a Read Only Memory (ROM), a Random Access Memory (RAM), and a hard disk. The storage 41 stores a program executed by the controller 42, which will be described later. The storage 41 stores information on the driver's face direction angle, for example.

The controller 42 is a Central Processing Unit (CPU), for example. The controller 42 functions as an angle value calculation part 421, a determination part 422, and an alarm part 423 by executing the program stored in the storage 41. The controller 42 identifies the driver's face direction angle, and determines whether or not the driver is in the state of being inattentive to the road ahead.

The angle value calculation part 421 calculates the angle value on the basis of the captured image captured by the imaging device 1. The angle value calculation part 421 calculates the angle value indicating at least one of i) the driver's face direction angle in the yaw direction with respect to the traveling direction (FIG. 2B) or ii) the driver's face direction angle in the pitch direction with respect to the traveling direction (FIG. 2A). The angle value calculation part 421 notifies the determination part 422 about the calculated angle value.

The determination part 422 determines whether or not the driver is in the state of being inattentive to the road ahead on the basis of whether or not the integrated value of the angle values in a past predetermined first determination period is equal to or greater than the first threshold value. The determination part 422 makes a determination at a predetermined time interval (for example, one second interval). A first determination period is a predetermined period starting from each time point at when the determination part 422 makes a determination. A first threshold value is a value predetermined by experiment as the maximum value of the integrated values during the first determination period corresponding to how the driver moves his/her face at a level that does not cause a problem in terms of safety, for example.

The determination part 422 determines that the driver is in the state being inattentive to the road ahead if the integrated value of the angle values in the past predetermined first determination period is equal to or greater than the first threshold value and the angle value of the driver at the present moment is equal to or greater than a second threshold value. On the other hand, even if the integrated value of the angle values in the past predetermined first determination period is equal to or greater than the first threshold value, the determination part 422 does not determine that the driver is in the state of being inattentive to the road ahead if the angle value of the driver at the present moment is less than the second threshold value. The second threshold value is a value predetermined by experiment as the maximum value of the angle value at a level that does not cause a problem in terms of safety, for example.

Figure 3A:
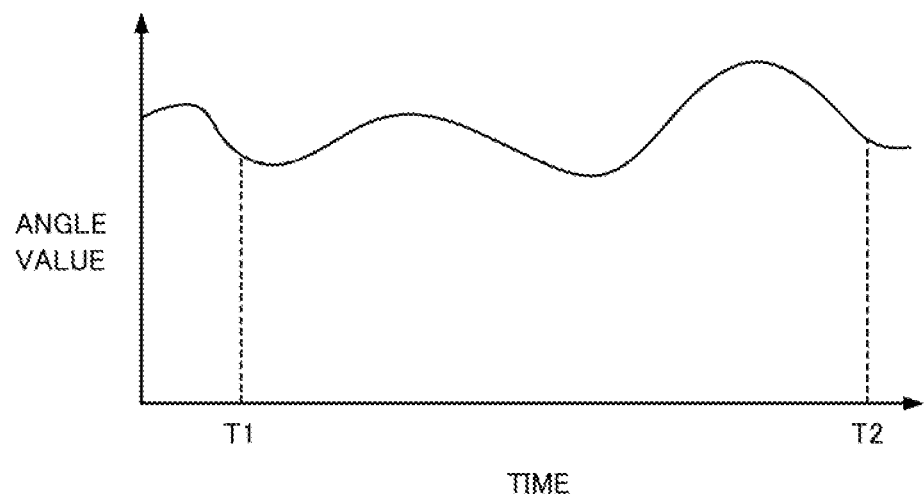
FIG. 3A shows a relationship between i) a time when a determination part 422 determines whether or not the driver is in a state of being inattentive to the road ahead and ii) an angle value and an integrated value indicating a driver's face direction.
Figure 3B:
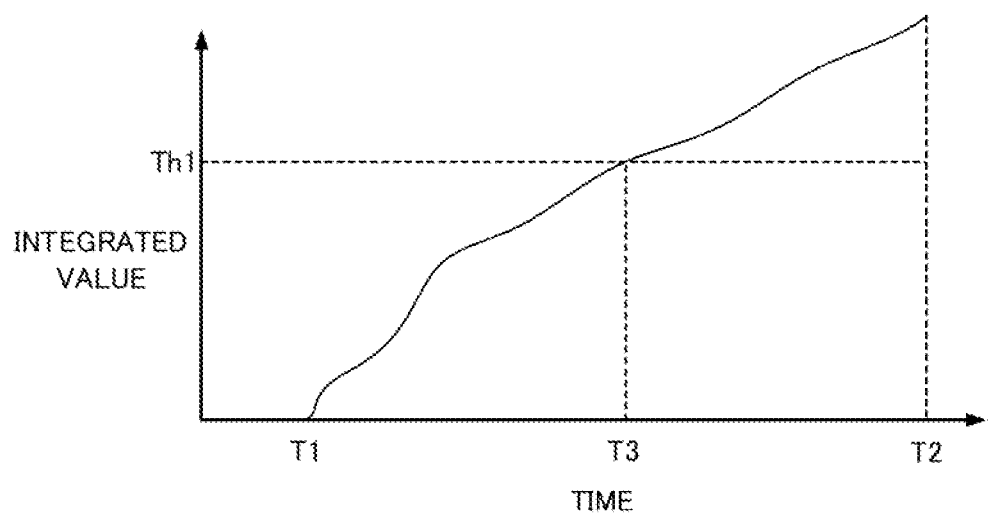
FIG. 3B shows a relationship between i) a time when a determination part 422 determines whether or not the driver is in a state of being inattentive to the road ahead and ii) an angle value and an integrated value indicating a driver's face direction.

FIGS. 3A and 3B show a relationship between i) a time when the determination part 422 determines whether or not the driver is in the state of being inattentive to the road ahead and ii) the angle value and the integrated value indicating the driver's face direction. FIG. 3A shows the angle value for each time. The horizontal axis in FIG. 3A represents time, and the vertical axis in FIG. 3A represents the angle value indicating the driver's face direction for each time. A time T1 indicates the start time of the past predetermined first determination period corresponding to a time T2. The time T2 indicates the present moment. The period between the time T1 and the time T2, that is the past predetermined first determination period, is 10 seconds, for example.

FIG. 3B shows the integrated value of the angle values after the time T1. The horizontal axis in FIG. 3B represents time, and the vertical axis in FIG. 3B represents the integrated value of the angle values after the time T1. A time T3 indicates the time when the integrated value of the angle value becomes equal to a first threshold value Th1. The integrated value of the angle value at the time T3 is the integrated value of the angle values during the period from the time T1 to the time T3.

As described above, if the integrated value is equal to or greater than the first threshold value Th1 during the first determination period, the determination part 422 determines whether or not the driver is in the state of being inattentive to the road ahead on the basis of the angle value at the time T2.

Figure 4A:
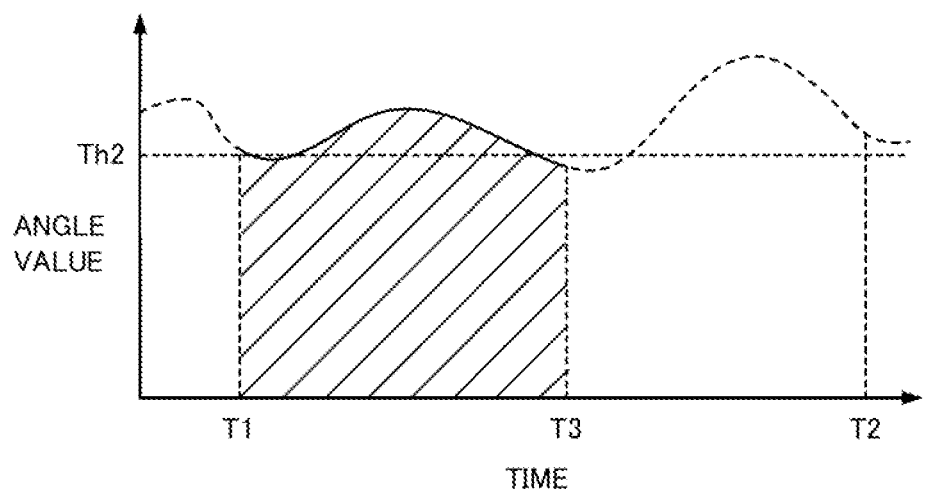
FIG. 4A illustrates a process of the determination part 422 determining whether or not a driver is in a state of being inattentive to the road ahead.
Figure 4B:
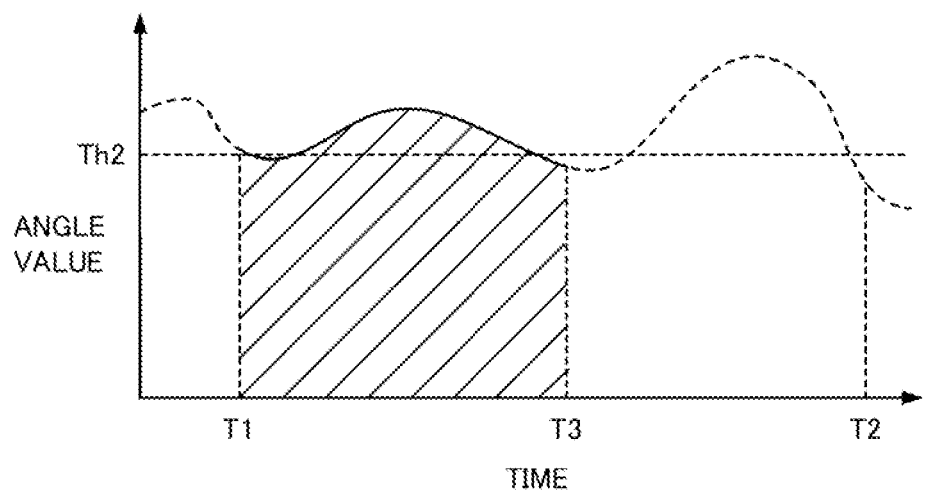
FIG. 4B illustrates a process of the determination part 422 determining whether or not a driver is in a state of being inattentive to the road ahead.

FIGS. 4A and 4B illustrate a process of the determination part 422 determining whether or not the driver is in the state of being inattentive to the road ahead. The horizontal axes in FIGS. 4A and 4B represent time, and the vertical axes in FIGS. 4A and 4B represent the angle value of the driver's face direction for each time. In the examples shown in FIGS. 4A and 4B, as shown in FIG. 3B, the integrated value of the angle values from the time T1 to the time T3 (hatched portions in FIGS. 4A and 4B) is equal to the first threshold value Th1.

FIG. 4A shows a change in the angle value in a case where the angle value at the time T2 is equal to or greater than a second threshold value Th2 after the integrated value reaches the first threshold value Th1 at the time T3. FIG. 4B shows a change in the angle value in ca case where the angle value at the time T2 is less than the second threshold value Th2 after the integrated value reaches the first threshold value Th1 at the time T3.

In the case of the example shown in FIG. 4A, the determination part 422 determines that the driver is in the state of being inattentive to the road ahead at the time T2 since the integrated angle value is equal to or greater than the first threshold value Th1 in the past predetermined first determination period (from the time T1 to the time T2) and the angle value at the time T2 is equal to or greater than the second threshold value Th2.

On the other hand, in the case of the example shown in FIG. 4B, the determination part 422 determines that the driver is not in the state of being inattentive to the road ahead since the integrated value of the angle values in the past predetermined first determination period is equal to or greater than the first threshold value Th1 but the angle value of the driver at the present moment is less than the second threshold value Th2. It should be noted that, if the integrated value of the angle values in the first determination period is less than the first threshold value Th1, the determination part 422 determines that the driver is not in the state of being inattentive to the road ahead regardless of the angle value at the present moment (the time T2).

The determination part 422 may determine the second threshold value Th2 on the basis of the speed of the vehicle S. Specifically, the determination part 422 may set the second threshold value Th2 to be smaller when the speed of the vehicle is high than when the speed of the vehicle is low. By having the determination part 422 determine the second threshold value Th2 in this manner, the safe driving determination apparatus 4 can make a stricter determination of whether the driver is in the state of being inattentive to the road ahead when the speed of the vehicle is high, which increases the danger to the driver, than when the speed of the vehicle is low.

If the determination part 422 determines that the driver of the vehicle S is in the state of being inattentive to the road ahead, the determination part 422 notifies the alarm part 423 that the driver is in the state of being inattentive to the road ahead. When the alarm part 423 receives a notification from the determination part 422 that the driver is in the state of being inattentive to the road ahead, the alarm part 423 notifies the alarm device 3 to issue an alarm.

By having the determination part 422 and the alarm part 423 operate in this manner, the determination part 422 determines that the driver is not in the state of being inattentive to the road ahead if the angle value of the driver's face direction at the present moment is less than the second threshold value Th2, even if the integrated value of the angle values during the past predetermined first determination period is greater than the first threshold value Th1. As a result, the safe driving determination apparatus 4 can restrict the alarm device 3 from issuing the alarm even though the driver is attentive in the road ahead at the present moment.

The determination part 422 may determine whether or not the driver is in the state of being inattentive to the road ahead on the basis of the result of comparing a statistical value (determination value) of the plurality of angle values in a second determination period, which is shorter than the first determination period, including the present moment, with a third threshold value. The statistical value is, for example, a value obtained by statistically processing the plurality of angle values within the second determination period and is a value indicating a tendency of the angle values within the second determination period. The value obtained by using the statistical processing is the average or median value of the plurality of angle values within the second determination period, for example. The third threshold is a value predetermined by experiment, for example.

Figure 5:
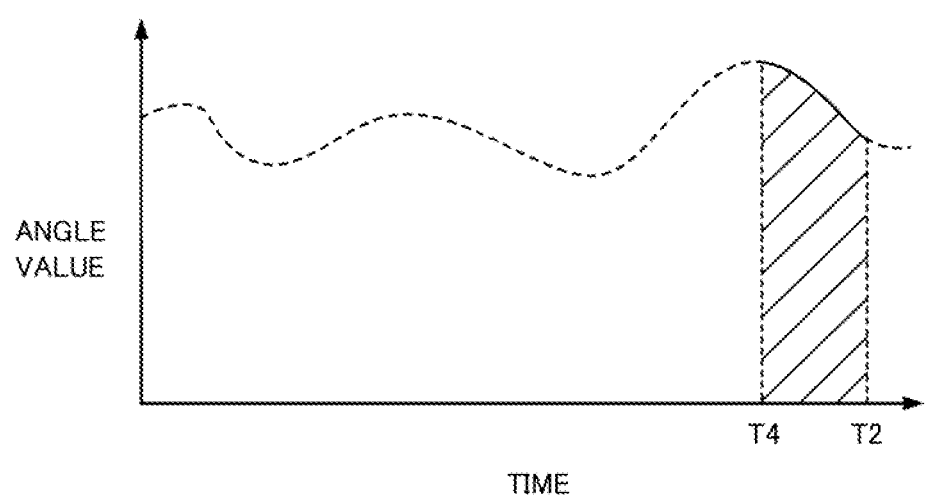
FIG. 5 shows a relationship between a second determination period including a present moment and an angle value.

FIG. 5 shows a relationship between a second determination period including the present moment and the angle value. FIG. 5 shows the second determination period including the present moment (period from a time T4 to the time T2, and is 1 second, for example). The horizontal axis of FIG. 5 represents the time, and the vertical axis of FIG. 5 represents the angle value indicating the driver's face direction at each time.

At the time T2, the determination part 422 does not determine that the driver is in the state of being inattentive to the road ahead even if the angle value at the time T2 is equal to or greater than the second threshold value Th2 if, for example, the statistical value based on the plurality of angle values within the second determination period is less than the third threshold value. By having the determination part 422 operate in this manner, the determination part 422 restricts the alarm device 3 from issuing the alarm due to the driver turning his/her face direction just for a moment at the time T3.

Further, the determination part 422 may determine the length of the second determination period including the present moment on the basis of the speed of the vehicle at the present moment. Specifically, for example, if the speed of the vehicle is high, the determination part 422 may determine the second determination period to be shorter than when the speed of the vehicle is low. By having the determination part 422 determine the second determination period to be short in this manner, the safe driving determination apparatus 4 can be more sensitive to changes in the driver's face direction if the speed of the vehicle high, which increases the driver's risk, than when the speed of the vehicle is low.

Furthermore, the determination part 422 may determine the third threshold value on the basis of the speed of the vehicle at the present moment. Specifically, the determination part 422 may set the third threshold value smaller when the speed of the vehicle is high than when the speed of the vehicle is low. By having the determination part 422 determine the third threshold value in this manner, the safe driving determination apparatus 4 can make a stricter determination of whether the driver is in the state of being inattentive to the road ahead when the speed of the vehicle is high, which increases the danger to the driver, than when the speed of the vehicle is low.

<Effect of Safe Driving Determination Apparatus 4>

As described above, the controller 42 includes the angle value calculation part 421 that calculates the angle value in the face direction of the driver of the vehicle S, and the determination part 422 that determines whether or not the driver is in the state of being inattentive to the road ahead on the basis of the calculated angle value. The determination part 422 does not determine that the driver is in the state of being inattentive to the road ahead if the integrated value of the plurality of angle values in the past predetermined period calculated by the angle value calculation part 421 is equal to or greater than the first threshold value and if the angle value at the present moment is less than the second threshold value.

Therefore, in the case where the driver is not in the state of being inattentive to the road ahead at the present moment, the alarm device 3 does not issue the alarm even if the driver was in the state of being inattentive to the road ahead for a certain period of time in the past. Accordingly, the safe driving determination apparatus 4 can prevent or reduce the issuance of the alarm if the driver is not in the state of being inattentive to the road ahead at the present moment.

The present disclosure is explained on the basis of the exemplary embodiments. The technical scope of the present disclosure is not limited to the scope explained in the above embodiments and it is possible to make various changes and modifications within the scope of the disclosure. For example, all or part the apparatus can be configured with any unit which is functionally or physically dispersed or integrated. Further, new exemplary embodiments generated by arbitrary combinations of them are included in the exemplary embodiments of the present disclosure. Further, effects of the new exemplary embodiments brought by the combinations also have the effects of the original exemplary embodiments.

DESCRIPTION OF SYMBOLS 1 imaging device
3 alarm device
4 safe driving determination apparatus
41 storage
42 controller
421 angle value calculation part
422 determination part
423 alarm part

The invention claimed is:

1. A safe driving determination apparatus for acquiring an angle value indicating a face direction angle of a driver by using a traveling direction of a vehicle as a reference after capturing an image of the driver of the vehicle with an imaging device to determine whether or not the driver is in a state of being inattentive to a road ahead on a basis of the acquired angle value, the apparatus comprising:
   an angle value calculation part that calculates an angle value indicating a face direction angle of at least one of i) a face direction angle of the driver in a yaw direction with respect to the traveling direction or ii) a face direction angle of the driver in a pitch direction with respect to the traveling direction; and
   a determination part that:
      determines that the driver is in a state of being inattentive to the road ahead if an integrated value of angle values during a past predetermined first determination period is equal to or greater than a first threshold value and an angle value of the driver is equal to or greater than a second threshold value at a present moment; and
      does not determine that the driver is in a state of being inattentive to the road ahead if the angle value of the driver is less than a second threshold value at the present moment, even if an integrated value of angle values during a past predetermined first determination period is equal to or greater than a first threshold value,
   wherein the determination part does not determine that the driver is in the state of being inattentive to the road ahead even if the angle value at a second determination period, which is shorter than the first determination period, including the present moment, is equal to or greater than the second threshold value if a statistical value based on the angle values within the second determination period is less than a third threshold value.

2. The safe driving determination apparatus according to claim 1, wherein, if the statistical value of the angle values in the second determination period is less than the third threshold value, the determination part does not determine that the driver is in a state of being inattentive to the road ahead even if the angle value is equal to or greater than the first threshold value.

3. The safe driving determination apparatus according to claim 1, wherein the determination part determines a length of the second determination period on the basis of a speed of the vehicle at the present moment.

4. The safe driving determination apparatus according to claim 1, wherein the determination part determines a length of the second determination period to be shorter when speed of the vehicle is high than when the speed of the vehicle is low.

5. The safe driving determination apparatus according to claim 1, wherein the determination part determines the third threshold value on the basis of a speed of the vehicle at the present moment.

6. The safe driving determination apparatus according to claim 1, wherein the determination part sets the third threshold value smaller when a speed of the vehicle is high than when the speed of the vehicle is low.

\* \* \* \* \*